US009168273B2

(12) United States Patent
Dracker

(10) Patent No.: US 9,168,273 B2
(45) Date of Patent: Oct. 27, 2015

(54) INTRATHECAL ADMINISTRATION OF AUTOLOGOUS STEM CELLS TO TREAT INTRAVENTRICULAR HEMORRHAGE IN PREMATURE INFANTS

(76) Inventor: Robert A. Dracker, Liverpool, NY (US)

( * ) Notice: Subject to any disclaimer, the term of this patent is extended or adjusted under 35 U.S.C. 154(b) by 888 days.

(21) Appl. No.: 12/718,612

(22) Filed: Mar. 5, 2010

(65) Prior Publication Data

US 2010/0226896 A1    Sep. 9, 2010

Related U.S. Application Data

(60) Provisional application No. 61/157,712, filed on Mar. 5, 2009.

(51) Int. Cl.
*A61K 35/545* (2015.01)
*A61K 35/51* (2015.01)

(52) U.S. Cl.
CPC .............. *A61K 35/545* (2013.01); *A61K 35/51* (2013.01)

(58) Field of Classification Search
None
See application file for complete search history.

(56) References Cited

U.S. PATENT DOCUMENTS 6,753,350 B1 *  6/2004  Hansen et al. ................ 514/560
2008/0131405 A1 *  6/2008  Jeun ............................ 424/93.7

* cited by examiner

*Primary Examiner* — Blaine Lankford
(74) *Attorney, Agent, or Firm* — Blaine T. Bettinger; George R. McGuire; Bond Schoeneck & King

(57) ABSTRACT

The invention provides a method of treating a premature infant at a statistical risk of sustaining an intraventricular hemorrhage. The method, or therapeutic protocol, can include at least one or more of the following steps: identifying premature infants at a statistical risk of having an intraventricular hemorrhage, collecting umbilical cord blood from the identified premature infant, separating totipotential stem cells (e.g., having the ability to proliferate and differentiate as neural stem cells) from the collected cord blood, storing the separated stem cells, establishing evidence of an intraventricular hemorrhage (preferably prior to Grade III/IV if possible) in the premature infant, and intrathecally administering the autologous cord blood derived stem cells to the premature infant.

14 Claims, 3 Drawing Sheets

INTRATHECAL ADMINISTRATION OF AUTOLOGOUS STEM CELLS TO TREAT INTRAVENTRICULAR HEMORRHAGE IN PREMATURE INFANTS

CROSS-REFERENCE TO RELATED APPLICATIONS

The present invention claims priority to U.S. Provisional Application No. 61/157,712, filed Mar. 5, 2009, which is incorporated by reference herein in its entirety.

BACKGROUND OF THE INVENTION

1. Field of the Invention

The present invention relates to a method for administering autologous stem cells in premature infants and, more particularly, to a method for intrathecal administration of autologous cord blood derived stem cells in premature infants sustaining intraventricular hemorrhages.

2. Description of the Related Art

Despite advances in the science of neonatal care and support of younger gestational age infants, these infants are at increasingly greater post-natal risks associated with their physiologic prematurity. It is well recognized that the incidence of peri- and intra-ventricular hemorrhage (IVH) is inversely proportional to gestational age. Although the incidence of hemorrhages in very low birth weight infants (<1500 grams) or in those less than 34 weeks gestation has been reported to be as great as 50 percent, the actual incidence in recent years has greatly improved to somewhere between 10 and 20 percent (although no firm data with regards to actual numbers or severity can be estimated). Improvements in and the availability of perinatal and postnatal care of these infants, as well as the use of indomethacin have contributed to the significant benefits recognized. However, it has been suggested that the actual number of premature infants who survive following an intraventricular hemorrhage is increasing since greater than 85% of infants between 700-1500 grams now survive. The risk of death and/or short term and long term complications to these premature infants, however, still exists.

Over 90 percent of intraventricular hemorrhages in premature infants occur within the first 72 hours of life, are most likely associated with physiologic changes within the premature neuro-circulation of the subependymal germinal matrix, as well as the potential contributing roles of abnormalities in primary and secondary hemostasis and other metabolic stress factors such as acidosis, oxygenation (hypoxia), intravascular nitric oxide and hydrogen sulfide levels and free oxygen radical formation. The initial signs and symptoms of an intraventricular hemorrhage are readily recognized by those routinely caring for the premature and include: apnea and hypoventilation, bradycardia, anemia, seizures, decreased muscle tone and activity, and a bulging anterior fontanel.

The diagnosis of an intraventricular hemorrhage is initially confirmed by a cranial ultrasound, usually performed in a serial manner to determine the extent, grade and progression of the hemorrhage (grades I-IV, as discussed infra). Alternative diagnostic considerations include the presence of sepsis, a pneumothorax (ventilated premature infant), cardiac disease, seizure activity, and/or metabolic and electrolyte disturbances.

Intracranial hemorrhages are classified into four grades, I-IV (as should be appreciated by those skilled in the art). These grades are defined by the severity of the hemorrhage as follows: Grade I—Hemorrhage limited to the subependymal matrix; Grade II—Hemorrhage extending into the ventricular system (<50%) without acute ventriculomegaly; Grade III—Hemorrhage extending into the ventricular system with acute dilatation due to "flooding" of 50% or more of one or both of the lateral ventricles; and Grade IV—Hemorrhage of grades I, II or III with extension into the brain parenchyma.

Although most hemorrhages are mild in nature, described as either grades I or II, and are associated with mild sequelae; hemorrhages of grades III and IV typically result in primary and secondary damage to the brain parenchyma and are associated with significant short term (e.g., post-hemorrhagic hydrocephalus) and long term complications (Grade III/IV sequelae include: hydrocephalus frequently requiring shunting, seizures, developmental delay and mental retardation, porencephalic cyst formation and cerebral palsy). The pathogenesis of a Grade III/IV hemorrhage seems to differ significantly from the other lesser grades, appearing to result from hemorrhagic venous infarctions surrounding the terminal vein and feeder vessels, most likely related to increased venous pressure following or associated with the development of a lower grade hemorrhage. In most cases the medical management of hydrocephalus is necessary and a severe hemorrhage imparts significant co-morbid effects on the general care of the infant, involving their cardio-respiratory management and seizure control. The parenchymal damage caused by a Grade III/IV intracranial hemorrhage results in tissue necrosis and non-neuronal cyst formation. Non-neuronal cysts can evolve to become contiguous with adjacent ventricles leading to the formation of a porencephalic cyst (see FIG. 1). Such conditions can result in the secondary neurologic diagnosis of cerebral palsy, with or without mental retardation and seizures (as noted supra).

It should be noted that the structural damage of a severe hemorrhage, Grade III/IV hemorrhages, commonly affect the integrity and cellularity of the germinal matrix. The germinal matrix is the primary location of glial cell precursors (neuroblasts & glioblasts). Glial cell precursors have demonstrated to have proliferative potential following stroke or brain injury in adults. These precursors have also demonstrated stem cell plasticity and multipotential characteristics, including their ability to differentiate into hematopoietic stem cells.

Conventional methods of prevention of intraventricular hemorrhages and severity mitigation include indentifying at-risk infants, minimizing contributing factors, early identification, and pharmaco-protectants such as antioxidants, and COX inhibitors. Supportive therapy for the post-IVH child includes seizure control, shunt care and maintenance, developmental therapy, sensory deficit care, special education, and lifelong support, each of which can cause financial and social burdens and psychosocial issues.

SUMMARY OF THE INVENTION

The present inventions recognizes that there are potential problems and/or disadvantages with the conventional methods of prevention of intraventricular hemorrhages and severity mitigation, coupled with the natural postnatal, post-traumatic neurologic functional neurological healing. One potential problem is that the care for an infant who has sustained a severe intraventricular hemorrhage is supportive at best, and is associated with the expectations that the child will have obvious subsequent developmental disabilities, the potential for lifelong seizures, and the reliance on supportive services and intervention for the duration of their lives. A related potential problem is that the natural postnatal, post-traumatic neurologic functional neurological healing of not only structural brain parenchyma but the surrounding endothelial-vascular components as well, results in "healing" in a "non-functional" manner. This "healing" may interfere with normal neural pathways, which are critical for ongoing neuro-development. Various embodiments of the present invention may be advantageous in that they may solve or reduce one or more of the potential problems and/or disadvantages discussed above in this paragraph.

It is therefore a principal object and advantage of the present invention to improve the pathophysiology of intraventricular hemorrhages and facilitate the prevention and potentially lessen the severity of brain insult and sequelae caused by such hemorrhages.

It is another object and advantage of the present invention to provide an effective therapeutic modality that is available once a neurologic insult has occurred. In particular, it is an object and advantage of the present invention to provide a therapeutic modality that is capable of providing postnatal, post-traumatic functional neurological healing of the structural brain parenchyma and the surrounding endothelial-vascular components.

In accordance with the foregoing objects and advantages, an embodiment of the present invention provides a method for intrathecal administration of autologous cord blood derived stem cells in premature infants sustaining intraventricular hemorrhages (as further discussed in the Detailed Description section). In short, the intrathecal administration of autologous cord blood derived stem cells (e.g., mesenchymal or CD34/lin−) can be performed as soon as a significant Grade IV or perhaps Grade III hemorrhage is noted. Being prepared in sterile fashion and maintained at refrigerated temperatures, the risks of autologous cells in this setting can be minimized.

Circulating toti-potential and pluripotential stem cells found in the cord blood of the new born have become well recognized as a rich source of proliferative cells that can be utilized for both hematopoietic and mesenchymal (somatic) cell therapies (e.g., the "plasticity" and safety of cord blood derived stem cells, of either pluripotential or mesenchymal fractions, has been demonstrated to have potential value and limited toxicity in adult patients who have experienced traumatic brain injuries or a progressive neurologic process, such as amyotrophic lateral sclerosis). Since the most severe intraventricular hemorrhages occur within the first 72 hours of life, an embodiment of the present invention provides a method for the intrathecal administration of autologous stem cells in sever stage IV bleeds for which there are no other therapies other than long term supportive approaches, as discussed supra.

It should be noted that there are many reasons for the large numbers of circulating stem cells in a new born having multi-lineage potential including physiologic and traumatic birth stress, tissue damage homing effects (mesenchymal), and ductus arteriosus effect: minimizing pulmonary stem cell sequestration (See FIG. 2, as should be appreciated by those skilled in the art. It should be noted that In-Utero ductus arteriosus allows only 5-6% blood flow in the high vascular resistance pulmonary circulation). Within the first few hours of birth, however, the majority of these "reparative" cells are no longer present to an appreciable degree in the circulation of the new born, most likely being sequestered by the spleen and the liver. Additionally, pulmonary sequestration of stem cells, i.e., circulating stem cell sequestration and removal in the lung following birth (facilitated by the closure of the ductus arteriosus), has lead to inefficient systemic administration of stem cells (other than hematopoietic). Due to this sequestration of stem cells, tissue-specific mesenchymal stem cell therapies have had to rely upon afferent administration (arteriolar). The role of P-selectin and CD 49d receptors in pulmonary sequestration versus sites of tissue injury is an important consideration in that these receptors allow for the homing and potential sequestration of circulating stem cells. The advantages of administering cells intrathecally is that they can attach to the site of tissue damage while avoiding systemic circulation whereby they would be removed by the pulmonary vascular circuit and not be available for tissue healing. The pulmonary removal of circulating stem cells is most likely what limits the ability to administer therapeutic stem cells in the general systemic circulation as a therapeutic modality. All previous attempts to utilize stem cell therapy for a specific site of tissue damage of dysfunction have relied upon the direct administration of the stem cells into the tissue directly by direct placement or injection which is technically difficult or by injecting them into the afferent arteriolar circulation. It can be considered that the birthing process itself represents the most universally experienced traumatic event in all newborns, commonly associated with some form of tissue damage, hemorrhage or associated cytopenia. Developmentally, the presence of these innate, therapeutic circulating toti-potential and pluripotential stem cells at the time of birth would seem to be beneficial to the survival of the newborn. Unfortunately, postnatal insults, such as an intraventricular hemorrhage occurs at a time when the availability of such cells is severely limited. Thus, an embodiment of the present invention provides a method of treating premature infants at a statistical risk of having a significant neurologic event that includes the collection and particular administration of autologous cord blood stem cells, as described herein.

In accordance with a further embodiment of the present invention, a method for intrathecal administration of autologous cord blood derived totipotential stem cells (having the ability to proliferate and differentiate as neural stem cells) in premature infants sustaining intraventricular hemorrhages is provided. The method utilizes a stem cell source which contains cells that demonstrate neuronal differentiation, i.e., mesenchymal cell origin (CD13+/CD29+/cd44+), and non-hematopoietic origin (CD34−/CD11a−/CD11b−). It is useful to note that factors which facilitate and cause neuronal cell marker expression include: fibroblast growth factor (bFGF), human epidermal growth factor (HEGF), retinoic acid, nerve growth factor (NGF), and brain derived neurotrophic factor (BDNF). Markers of neuronal-specific expression by mesenchymal cord blood stem cells include: beta-tubulin III (TuJ1), glial fibrillary acidic protein (GFAP), galactocerebroside (Gal-C): ologodendrocyte cell surface marker, nestin and doublecortin expression (very specific markers of multipotent neural stem cells), neurofilament, and other neuronal markers including: glypican 4, pleiotrophin mRNA, needin, musashi-1. Stem cell-derived neural related phenotypes include: neurons, astroglia, oligodendrocytes, endothelial/epithelial cells, and ependymal cells (each of which are needed for neural tissue repair and remodeling).

Further benefits of a method of an embodiment of the present invention include one or more of the following: intravascular or direct implantation of cord blood mesenchymal stem cells into areas of brain parenchymal damage have demonstrated engraftment, proliferation and functional differentiation; platelet activation at the IVH site results in P-selectin and CD 49d receptor expression facilitating "homing"; cerebrospinal fluid (CSF) itself supports cortical cell viability and proliferation; CSF milieu is contiguous with the site of injury (i.e., neurologic insult); is not vulnerable to pulmonary sequestration of stem cells and avoids circulatory removal and sequestration of CD49d+ stem cells (as discussed supra); ease of access and procedural administration; and mimics a perinatal process at a postnatal time frame using the same therapeutic cell population (a "resetting of the clock!").

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 1:
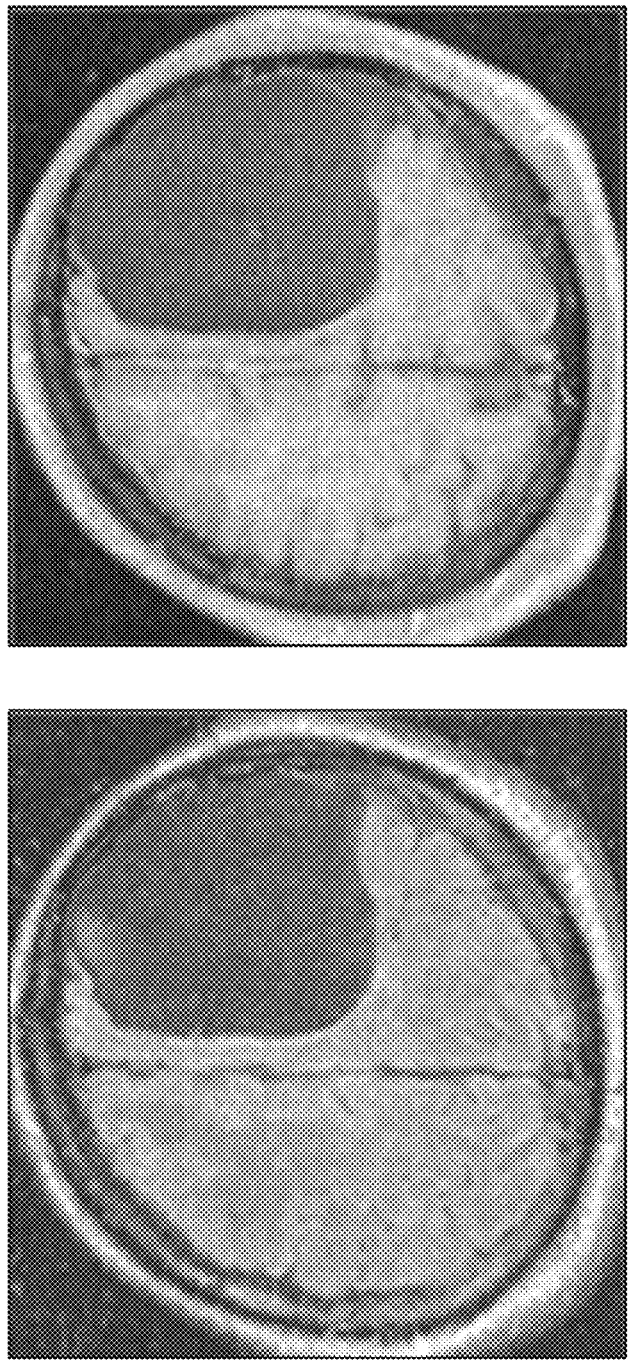
FIG. 1 is an computed tomography (CT) scan showing of a porencephaliuc cyst.
Figure 2:
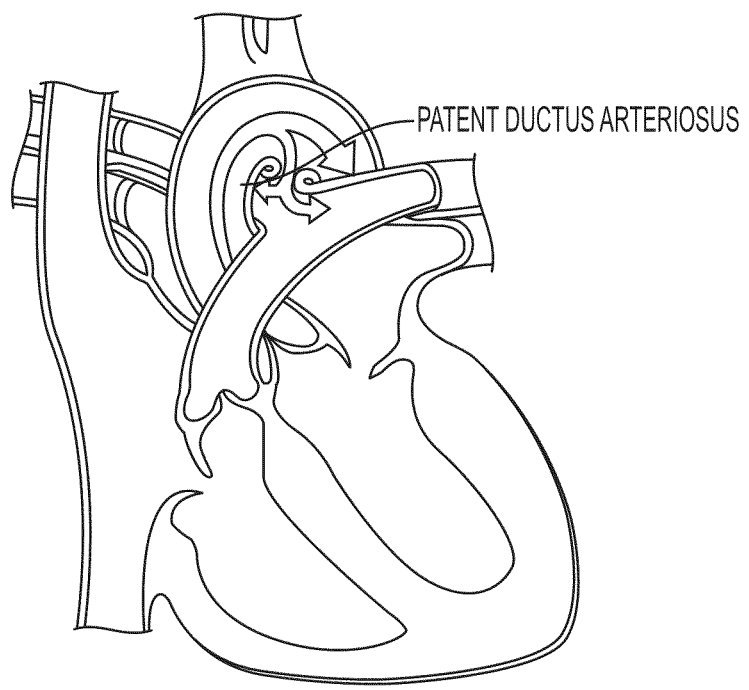
FIG. 2 is an illustration showing the patent ductus arteriosus effect.

The present invention will be more fully understood and appreciated by reading the following Detailed Description in conjunction with the accompanying drawings, wherein like reference numerals refer to like components.

Figure 3:
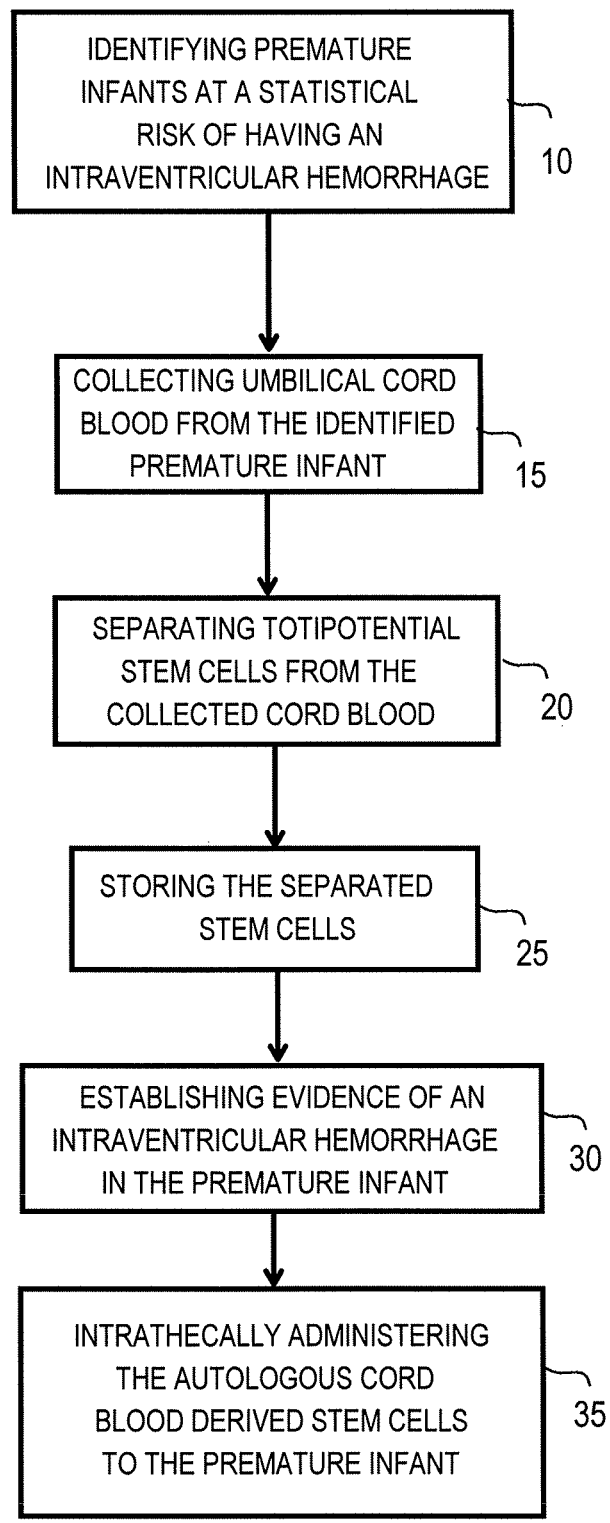
FIG. 3 is a flow chart illustrating steps involved in practicing a method for intrathecal administration of autologous cord blood derived stem cells in premature infants sustaining intraventricular hemorrhages, according to an embodiment of the present invention.

FIG. 3 is a flow chart illustrating steps involved in practicing a method for intrathecal administration of autologous cord blood derived stem cells in premature infants sustaining intraventricular hemorrhages, according to an embodiment of the present invention. The method, or therapeutic protocol, can include one or more of the following steps: identifying premature infants at a statistical risk of having an intraventricular hemorrhage 10, collecting umbilical cord blood from the identified premature infant 15, separating totipotential stem cells (having the ability to proliferate and differentiate as neural stem cells) from the collected cord blood 20, storing the separated stem cells 25, establishing evidence of an intraventricular hemorrhage (preferably prior to Grade III/IV if possible) in the premature infant 30, and intrathecally administering the autologous cord blood derived stem cells to the premature infant 35.

The step of identifying 10 can include identifying an under 1500 grams and/or under 34 week (preferably under 30 week) gestational age newborn, and the step of collecting can include collecting umbilical cord blood from such a newborn. The step of separating can include mesenchymal cell separation using semi-automated cell sorting separation or adherent cell culture technique. The step of separating can be followed by cellular phenotyping of the mesenchymal stem cell population, and aseptic cell suspension using autologous *cryoprecipitate-poor plasma (fibronectin depleted) and CPDA. The step of storing can include storing the separated stem cells at room temperature in Trimellitate plasticised platelet storage bags for up to 7 days. A mesenchymal cell concentration preparation can be used for the intrathecal procedure. Alternatively, an unmodified mononuclear cell suspension concentrate that contains both hematopoietic and mesenchymal cells can be used. The stem cell dose can be: $1\times10^5$ cells per dose (cell suspension volume of 0.5 ml). The step of intrathecally administering can include performing an aseptic lumbar puncture with free flowing CSF—withdrawing 0.5 ml into cell suspension syringe to admix and then slowly infusing 1 ml total intrathecally.

In accordance with an alternative embodiment of the present invention, cord blood may be collected and stored pursuant to the method and apparatus as described in U.S. Pat. No. 5,356,373, which is hereby incorporated by reference in its entirety herein.

The method of an embodiment of the present invention can provide a reparative and regenerative therapy for a CNS parenchymal event known to be associated with significant morbidity and mortality for which no other therapy exists other than supportive measures.

The method of an embodiment of the present invention may be used as a treatment of adults (e.g., as a treatment after a stroke or other injury).

The method of an embodiment of the present invention may be used as a treatment of infants suffering from traumatic brain injury or cerebral palsy during the birthing process.

While the invention is susceptible to various modifications, and alternative forms, specific examples thereof have been shown in the drawing and are herein described in detail. It should be understood, however, that the invention is not to be limited to the particular forms or methods disclosed, but to the contrary, the invention is to cover all modifications, equivalents and alternatives falling within the spirit and scope of the present invention.

DEFINITIONS

The following definitions are provided to facilitate claim interpretation:

Present invention: means at least some embodiments of the present invention; references to various feature(s) of the "present invention" throughout this document do not mean that all claimed embodiments or methods include the referenced feature(s).

First, second, third, etc. ("ordinals"): Unless otherwise noted, ordinals only serve to distinguish or identify (e.g., various members of a group); the mere use of ordinals implies neither a consecutive numerical limit nor a serial limitation.

To the extent that the definitions provided above are consistent with ordinary, plain, and accustomed meanings (as generally shown by documents such as dictionaries and/or technical lexicons), the above definitions shall be considered supplemental in nature. To the extent that the definitions provided above are inconsistent with ordinary, plain, and accustomed meanings (as generally shown by documents such as dictionaries and/or technical lexicons), the above definitions shall control. If the definitions provided above are broader than the ordinary, plain, and accustomed meanings in some aspect, then the above definitions shall be considered to broaden the claim accordingly.

To the extent that a patentee may act as its own lexicographer under applicable law, it is hereby further directed that all words appearing in the claims section, except for the above-defined words, shall take on their ordinary, plain, and accustomed meanings (as generally shown by documents such as dictionaries and/or technical lexicons), and shall not be considered to be specially defined in this specification. In the situation where a word or term used in the claims has more than one alternative ordinary, plain and accustomed meaning, the broadest definition that is consistent with technological feasibility and not directly inconsistent with the specification shall control.

Unless otherwise explicitly provided in the claim language, steps in method steps or process claims need only be performed in the same time order as the order the steps are recited in the claim only to the extent that impossibility or extreme feasibility problems dictate that the recited step order (or portion of the recited step order) be used. This broad interpretation with respect to step order is to be used regardless of whether the alternative time ordering(s) of the claimed steps is particularly mentioned or discussed in this document.

What is claimed is:

1. A method of treating an intraventricular hemorrhage, said method comprising the steps of:
   a. identifying a premature infant at risk of having an intraventricular hemorrhage;
   b. collecting umbilical cord blood from the identified premature infant;
   c. separating a mononuclear cell fraction containing mesenchymal stem cells from the collected cord blood;
   d. confirming a need for treatment by establishing evidence of an intraventricular hemorrhage in the identified premature infant; and
   e. treating the premature infant by intrathecally administering at least a Portion of the autologous cord blood derived mononuclear cell fraction.

2. The method of claim 1, further comprising the step of storing the separated mononuclear cell fraction prior to the step of intrathecally administering the autologous cord blood derived mononuclear cell fraction.

3. The method of claim 1, wherein the step of identifying further comprises the step of identifying a premature infant who weighs under 1500 grams.

4. The method of claim 1, wherein the step of identifying further comprises the step of identifying an under 34 week gestational age premature infant.

5. The method of claim 1, wherein the autologous cord blood derived mononuclear cell fraction comprises cells that demonstrate neuronal differentiation.

6. The method of claim 1, wherein the mesenchymal cells comprise at least one of the following cells: CD13+, CD29+, and CD44+.

7. The method of claim 5, wherein the autologous cord blood derived mononuclear cell fraction comprises stem cells that are non-hematopoietic in nature.

8. The method of claim 7, wherein the non-hematopoietic cells comprise at least one of the following cells CD34−, CD11a−, and CD11b −.

9. The method of claim 5, further comprising the steps of:
   f. cellular phenotyping cells within the autologous cord blood derived mononuclear Cell fraction that demonstrate neuronal differentiation; and
   g. subjecting the cellular phenotyped cells to aseptic cell suspension.

10. The method of claim 2, wherein the step of storing can include storing the separated stem cells at room temperature in Trimellitate plasticised platelet storage bags for about one to seven days.

11. The method of claim 1, wherein the intrathecally administered autologous cord blood derived mononuclear cell fraction are administered to the identified premature infant in at least one dose comprising at least $1\times10^5$ cells per dose.

12. The method of claim 1, wherein the step of intrathecally administering comprises the steps of:
   f. performing an aseptic lumbar puncture with free flowing CSF;
   g. withdrawing about 0.5 ml of CSF into a syringe containing a cell suspension of autologous cord blood derived mononuclear cell fraction;
   h. admixing the CSF with the cell suspension; and
   i. infusing 1 ml total of the admixture intrathecally to the identified premature infant.

13. The method of claim 1, wherein the step of confirming a need for treatment comprises obtaining a clinical observation of said identified infant.

14. The method of claim 13, wherein said clinical observation is an ultrasound.

* * * * *